United States Patent [19]
Abonnenc

[11] 3,949,614
[45] Apr. 13, 1976

[54] AUTOMATIC VOLUMETRIC DEVICE FOR TAKING SAMPLES OF FLUID MATERIAL

[76] Inventor: Jean Abonnenc, 42, rue Laugier, 75017 Paris, France

[22] Filed: Nov. 21, 1974

[21] Appl. No.: 526,049

[30] Foreign Applicatin Priority Data

| Nov. 29, 1973 | France | 73.42631 |
|---|---|---|
| May 16, 1974 | France | 74.17116 |
| Oct. 17, 1974 | France | 74.34956 |

[52] U.S. Cl. .......................... 73/422 TC; 73/423 R
[51] Int. Cl.² .......................................... G01N 1/20
[58] Field of Search ........ 73/422 TC, 422 R, 421 B, 73/421 R, 423 R

[56] References Cited
UNITED STATES PATENTS

| 1,966,712 | 7/1934 | Fisher | 73/422 TC |
|---|---|---|---|
| 2,683,373 | 7/1954 | Gallup et al. | 73/422 |
| 3,066,539 | 12/1962 | Cooker et al. | 73/422 TC |

FOREIGN PATENTS OR APPLICATIONS

| 1,149,443 | 4/1969 | United Kingdom | 73/422 TC |
|---|---|---|---|

Primary Examiner—Richard E. Aegerter
Assistant Examiner—Willis Little
Attorney, Agent, or Firm—Haseltine, Lake & Waters

[57] ABSTRACT

Automatic volumetric apparatus for taking samples of fluid material, in particular in granular or powdered form, contained in a sampling zone, such as a hopper, where it is stored, either during treatment, or during conveyance, comprising a horizontal cylindrical probe having a longitudinal recess of trapezoidal section for the removal of a predetermined volume of material from the sampling zone, the probe being mounted to move inside a fixed closure member constituted by a sleeve co-axial to the probe. A drive unit drives the probe axially between a retracted position in which the recess is located in a discharge zone and an extension position in which the recess is located in the sampling zone. A guide rotates the probe with respect to the closure member in going between the extension position and the retracted position, so that the recess is directed respectively upwards and downwards, the closure member being provided with an aperture whose area is substantially equal to that of the opening of the recess and arranged so that it is in registry with the recess solely when the latter is in its retracted position for discharge. The probe is provided with a space at the front of the recess to prevent breakage of particles and transport thereof to the discharge zone.

8 Claims, 25 Drawing Figures

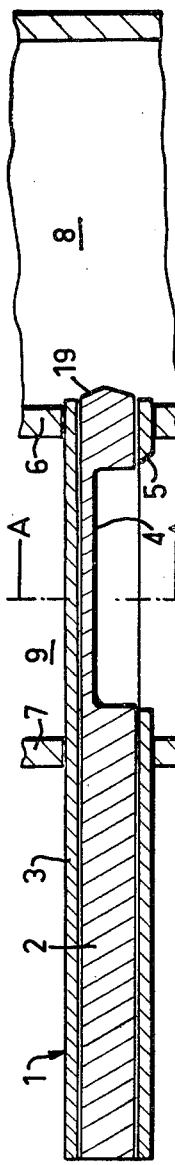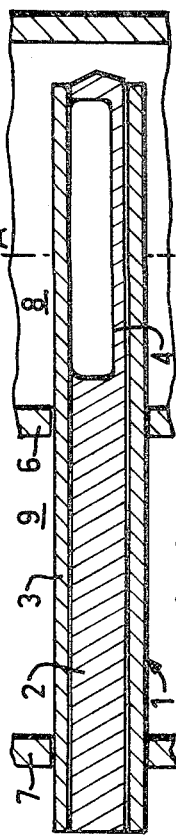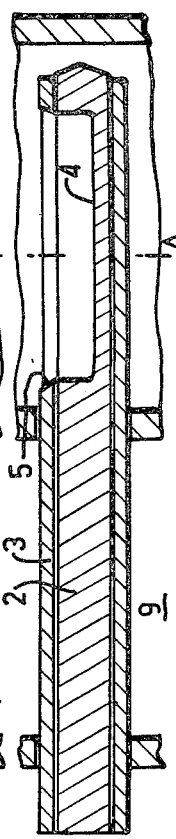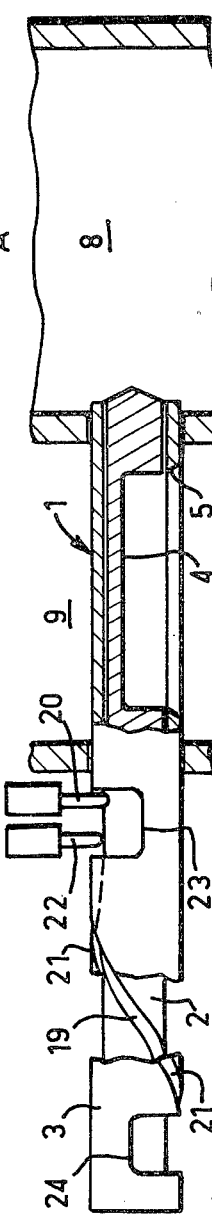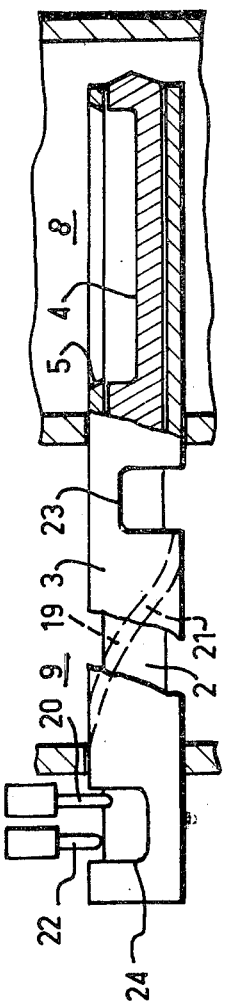
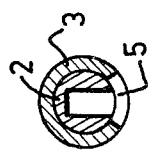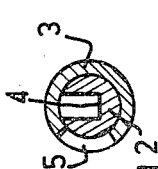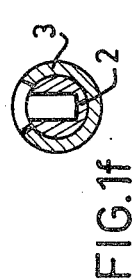

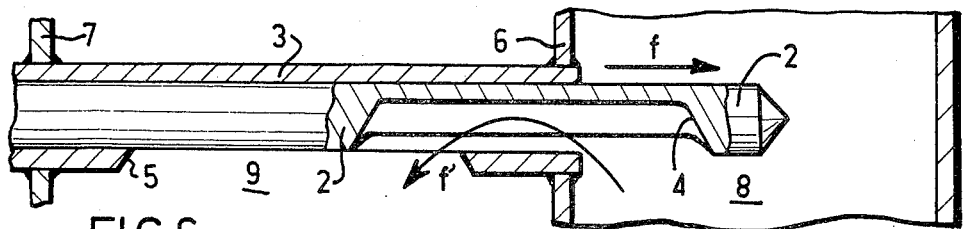
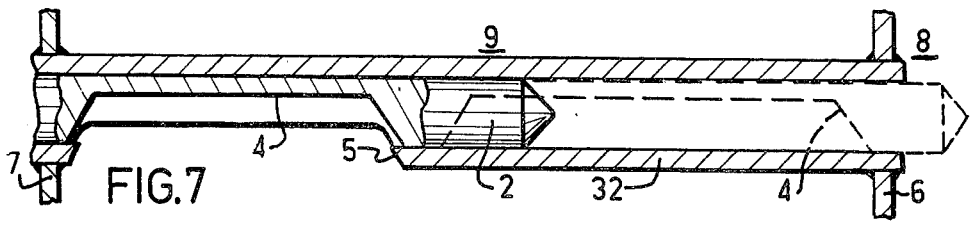
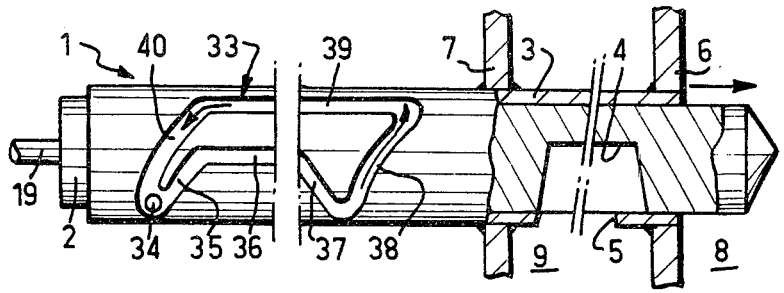
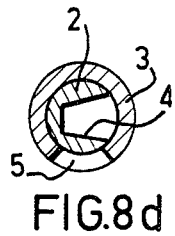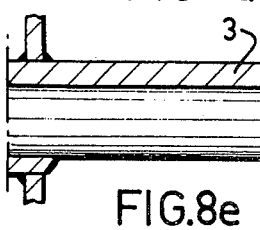
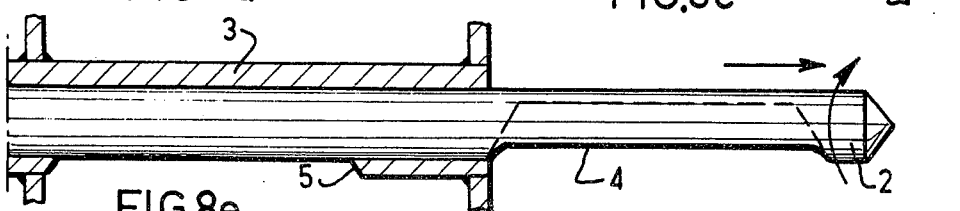
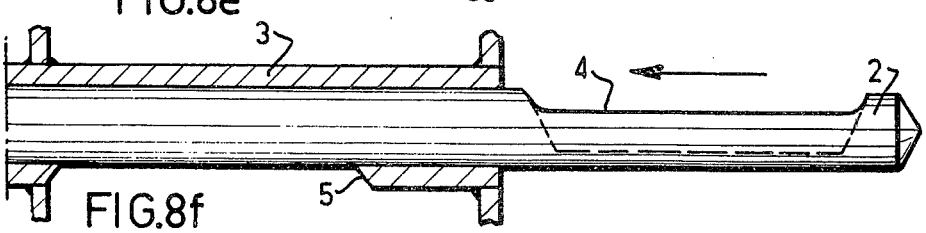

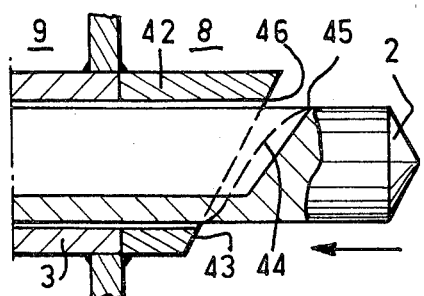
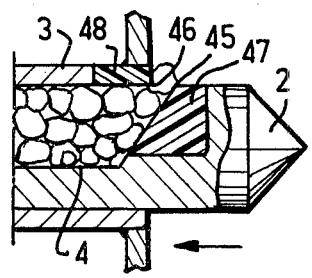
FIG.9  FIG.10
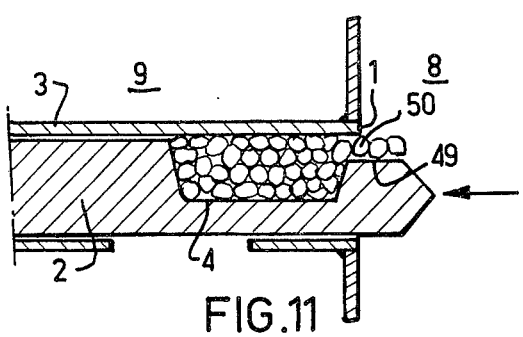
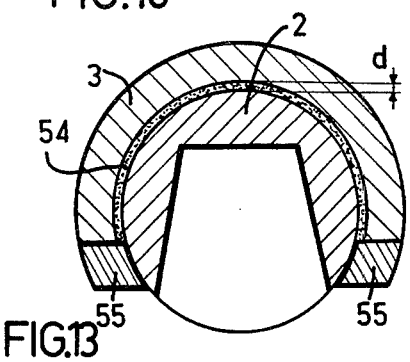
FIG.11  FIG.13
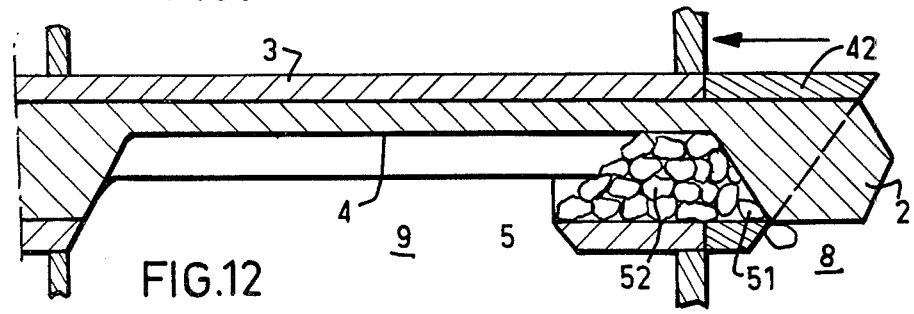
FIG.12
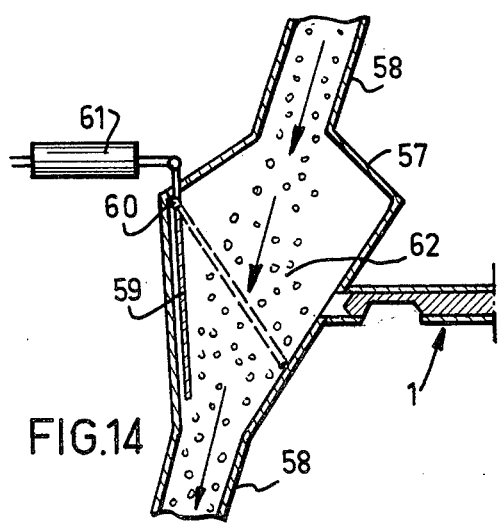
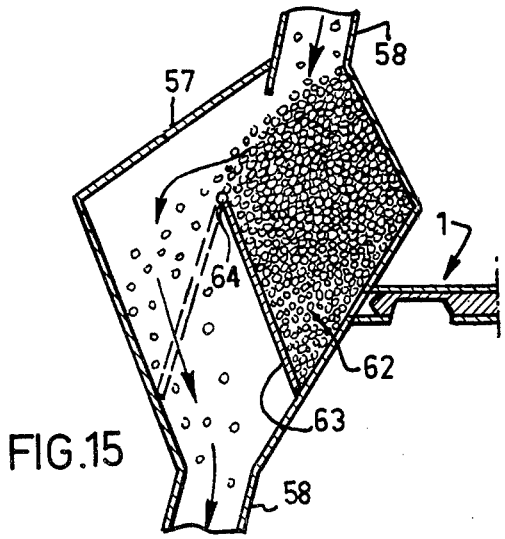
FIG.14  FIG.15

AUTOMATIC VOLUMETRIC DEVICE FOR TAKING SAMPLES OF FLUID MATERIAL

The present invention relates to an instantaneous action device for taking automatic volumetric samples of any fluid substance, in particular substances in granular or powdered form. In numerous industries, for example the agricultural, food or chemical industries, raw materials intended to become products which can be used or consumed by man, animals or by other industries are treated and transformed physically or chemically.

Most of these substances are in the form of grains, flour, powders, flakes, particles, in the agglomerated or liquid state, the composition or physical properties of which may vary according to their origins, the methods of transport, storage, chemical transformation, mixing and treatment of the material.

It will be understood that an inspection during all these operations is indispensable to ensure that the quality of the material treated conforms to the standards of manufacture and delivery as well as to commercial standards.

Since it is generally impossible to carry out a continuous inspection over the entire batch, there is no course other than to take samples in order to examine or analyze the substances. However, sampling must be undertaken in an accurate manner with a method and means which are strictly invariable and in an objective manner, preventing any human intervention in order that each sample taken is indisputably representative of the composition of the material inspected. Thus, the quality of the inspection of the conformity of the material depends on the quality of sampling.

Sampling methods known hitherto consist of operations carried out generally manually at indeterminate points and times, with manual apparatus of current usage such that the samples which are taken by these methods may always be disputed.

It is an object of the present invention to remedy these drawbacks by providing an automatic sampler, which makes it possible to take samples of constant volume remotely, at predetermined points and instantaneously, during the operations of receiving, despatching, handling, transforming, mixing, treating or conveying the material.

To this end, the sampler according to the invention is essentially characterized in that it comprises a horizontal cylindrical probe whose side wall has a longitudinal recess for sampling a predetermined volume of material, said probe being mounted to move inside a closure member constituted by a co-axial sleeve, drive means intended to drive at least the probe, in axial movement between a retracted position in which the recess is located in a discharge region such as a hopper outside said sampling region and an extension position in which the recess is located in said sampling region, guide means intended to rotate the probe with respect to the closure member, when it is located in its extension position and in its retracted position, in order that the recess is directed respectively upwards and downwards, the closure member being provided with a window whose surface is substantially equal to that of the opening of the recess and which is arranged to uncover the recess in the probe solely when the latter is in its extension position and retracted position.

Said drive means may be mechanical, electrical, hydraulic or pneumatic. Their actuation may be remotely controlled, programmed in advance outside the scope of any human intervention, which makes it possible for the sample obtained to be indisputable. It may also be undertaken on request, for example at the time of a simple electrical pulse.

According to a particular embodiment, the probe and closure member move together axially and are mounted to rotate one with respect to the other, said drive means being constituted by a double control, one ensuring penetration and withdrawal, as well as reversal of the probe and closure member arrangement, the other imparting an angular movement solely to the closure member to open and close it, the movements of said double control being appropriately synchronized to obtain the opening of the closure member at the times when the recess of the probe is in its above defined filling and emptying positions.

Owing to the closure member, it is possible to take samples in a relatively short time, which has the advantage of protecting the sample taken from other material in circulation, during the reversal and withdrawal of the probe in the sampling region.

Furthermore, contrary to known samplers, the sampler according to the invention has the advantage of leaving the circulation of material in the sampling region free, since it penetrates and remains in the latter solely during the time necessary for its filling, which is extremely short.

Said drive means may be constituted by a first hydraulic or pneumatic ram, the force of which is exerted along the axis of the sampler and by a second ram directed transversely with respect to the sampler and which is pivoted on the closure member. In a particular embodiment, the guide means are constituted, on the one hand, by a first helical groove formed through the wall of the closure member and in which is engaged a first lug integral with the frame of the apparatus and, on the other hand, by a second helical groove having an amplitude of approximately 180°, cut in the wall of the probe and in which engages a second lug also integral with the frame and which passes freely through the first helical groove formed on the closure member, the latter comprising a helical portion having an amplitude of approximately 180°, which may be superimposed on said second groove and is extended at its ends by two groove portions of such length and direction that they allow the closure member to continue to rotate, either to close or uncover the recess, as soon as the probe reaches the end of its travel, due to the abutment of the second lug against one of the ends of the second helical groove.

Thus, by starting from the inoperative position in which the sampler is outside the sampling region, with the recess directed downwards and closed by the closure member, the sampler receives a thrust which causes it to penetrate the sampling region. Simultaneously, the probe and closure member arrangement together undergoes a rotation of 180°. The probe becomes immobilized, the recess directed upwards, owing to the fact that the second lug abuts against the end of the second helical groove, but, under the thrust exerted by the drive means, the closure member alone continues its travel, rotating about the probe, until it uncovers the recess. The closure member is thus immobilized owing to the abutment of the first lug against the end of the first groove.

Advantageously, the drive means may be constituted by a single axial ram, the groove formed on the closure member thus having an amplitude of 180° increased by the angular amplitude necessary for the closure member to open.

In a variation, the closure member is fixed and has a window directed downwards, in the sampling region, the drive and guide means thus acting solely on the probe in order to bring it respectively into the sampling position and discharge position.

However, in this embodiment, it may happen that during the penetration of the probe, the recess, which is thus empty, establishes connection between the sampling region and the discharge region. Dust and fine particles which are foreign to the sample could thus infiltrate the discharge region and from there penetrate inside containers in which the samples are received. It is thus necessary to insulate the discharge region before, during and after sampling.

To remedy this drawback, according to the invention, the recess in the probe is disposed so that it never opens simultaneously into the sampling region and discharge region.

According to a first particular embodiment, this condition is satisfied by using a sampler whose closure member terminates adjacent the sampling region in a tubular portion whose wall is not recessed and the length of which is at least equal to the length of the recess of the probe.

According to another embodiment, the sampler comprises guide means, for example comprising a finger member and groove capable of rotating the probe with respect to the closure member, from the beginning of the penetration movement of the probe, through an angle sufficient for the recess to be closed by the wall of the closure member, said guide means then being able to retain the probe in this position during its penetration in the sampling region at least until the time when the rear edge of the recess projects beyond the front edge of the closure member window.

The Applicant has ascertained that during the withdrawal of the probe charged with a sample, it frequently happens that a grain of material of the sample wedges between the rear edge, in the direction of withdrawal, of the probe recess and the nose of the closure member which opens into the sampling region. If the wedged grain breaks and its debris passes with the sample, the latter will give erroneous indications regarding the physical properties of the material, for example the specific weight, appearance of the grains, crystals, pellets, granules or seeds, the percentage of broken grains etc.

Among the various solutions proposed according to the invention for avoiding this drawback and which will be described in the description, the following will be stated for the present: the front end of the probe, located in front of the recess, comprises a flat part or section having a depth greater than the size of grains of the material to be sampled.

Thus, at the end of the withdrawal movement of the probe, the flat part or section defines with the inner wall of the closure member, a space facilitating the liberation of the grains of material without them being crushed or destroyed. This arrangement is not detrimental to the seal of the sampler, since immediately after sampling and discharge, the probe is brought into the sealing position with respect to the closure member.

Another problem which the Applicant has encountered during the use of the sampler according to the invention, is that of entraining the material to be sampled, subsequent to the probe, which material remains at the end of the closure member, after the probe has completely withdrawn. Naturally, this material is expelled into the sampling region during the following extension movement of the probe. But, if, in the meantime, the material flowing in the circuit has been replaced by a different type of material expelled constitutes an impurity for this latter material which, in certain cases, particularly when sampling chemical, pharmaceutical or food products, is inadmissible even in very small quantities.

To remedy this drawback, the sampler is designed such that at the end of each sampling cycle, the probe is located in a position in which it fills the closure member over its entire length. In this manner, the terminal chamber of the closure member, which the grains of material may penetrate, is reduced to zero volume. A condition of this type may be fulfilled either by giving the front portion of the probe a length at least equal to the distance between the front edge of the opening of the closure member and the end of the latter, or by providing means for driving the probe, which advance the latter, after the sample has been discharged, by a length sufficient for the probe to fill the inner volume of the closure member.

According to an advantageous embodiment of the invention, a radial clearance is provided between the probe and the closure member, which is intended to reduce the frictional forces which may occur between these two parts in that sealing means are provided on the closure member and probe, constituted for example by two longitudinal lips fixed to the closure member on either side of the window and by annular gaskets making it possible to take up the clearance between the probe and closure member.

In the particular case where the material is not immobile, but is flowing in the discharge region, the sampler according to the invention cannot be used directly, since the distribution of material in the sampling region is not strictly uniform, in particular as regards the density and grain size. If sampling is undertaken without precautions, the sample will thus not be representative of the actual characteristics of the material.

To remedy such a drawback, a box is inserted in the flow circuit of the material, in which box the flow takes place by gravity, the flow being able to be provisionally stocked in the box, by means of at least one closure plate pivotally mounted about a horizontal shaft fixed to one wall of the box and being able to be moved by appropriate drive means between an open position and a position in which it completely closes the section of passage of the box, the sampler being filled in a wall of the box upstream of the plate.

Thus, in order to undertake sampling, the closure plate is closed in order to form with the walls of the box, a closed pocket in which the material which continues to arrive from upstream, is accummulated. Drive means synchronized with the movement of the closure plate are provided for actuating the sampler with a view to taking a sample of the material in said pocket.

However, in a device of this type, owing to a mechanical incident, it may happen that the stop plate jams in the closed position. Congestion of the circuit located upstream of the plate is thus produced.

This drawback is avoided according to the invention by using a box inserted in the material circuit such that the flow in the box takes place by gravity and a plate mounted to pivot about a horizontal shaft which passes through the space inside the box and which defines with the walls of the latter, two sections of passage located, one in the falling path of the material and the second offset with respect to said path, the plate being able to be brought either into the open position, by placing it in said second section of passage, or in the closed position in which it closes said first section of passage, the sampler being mounted to slide through the wall of the collecting pocket thus formed.

Congestion of the installation is prevented by a stopping device of this type, since even if the plate jams in the closed position, the overflow of the above described collecting pocket will empty over the top of the pivot shaft for the plate, into the second section of passage of the box and will thus discharge normally.

Several embodiments of the invention will now be described with reference to the accompanying drawings in which:

FIGS. 1a, 1c and 1e are diagrammatic views in axial section of a sampler according to a first embodiment, in three successive stages of a sampling cycle;

FIGS. 1b, 1d and 1f are respectively views in radial section on line A—A of the preceding FIGS.;

FIGS. 3 and 4 are elevational views, partially in axial section, of a sampler according to a second embodiment, respectively in the discharge position and in the position for taking a sample;

FIGS. 6 and 7 show in axial section, two other embodiments for taking a sample with a fixed closure member;

FIGS. 8a, 8c, 8e and 8f show in axial section, four successive positions during a sampling cycle, of a sampler according to yet another embodiment of the invention;

FIGS. 8b and 8d are respectively radial sectional views of FIGS. 8a and 8c;

FIGS. 9 to 11 are partial sectional views of samplers making it possible to solve the problem of jamming of the grains of material during the withdrawal of the probe, in three different ways;

FIG. 12 shows a sampler which makes it possible to avoid the transfer of broken portions of material grains, into the discharge region, subsequent to accidental jamming of the grains;

FIG. 13 is a diametral sectional view of a sampler provided with clearance between the probe and closure member and FIGS. 14 and 15 are two longitudinal sectional views of devices intended to interrupt the flow of material in a circuit, with a view to taking a sample.

Figure 2:
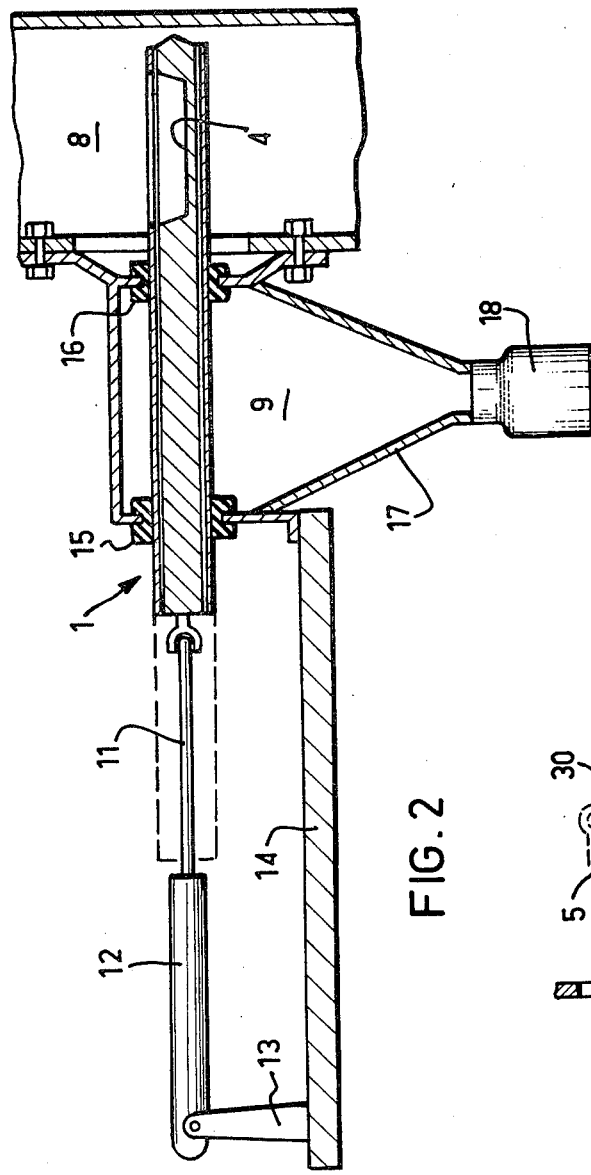
FIG. 2 is a sectional view of an actuating system which makes it possible to drive the sampler of the preceding FIGS. in axial movement.

Firstly, with reference to FIGS. 1a to 1f, the sampler 1 comprises a cylindrical probe 2 mounted to rotate inside a coaxial sleeve or closure member 3, under the action of appropriate drive means. The sampler is directed horizontally. On its lateral wall, in the vicinity of one end, the probe 2 has a recess 4 of predetermined volume and a sectional shape appropriate to the nature of the material to be sampled. For example, as shown in FIGS. 1b, 1d and 1f, the recess 4 has a substantially rectangular section. Such a shape is suitable for sampling a granular material having relatively good fluidity. On the other hand, if it is intended to take samples of flour or powder having poorer fluidity, this shape of the recess should be avoided, since there is a danger of it leading to a so-called arch effect, in which the material sticks to the walls such that the entire volume of material sampled cannot detach itself from the walls of the recess, when the latter is directed downwards. It is thus more appropriate to use a sampler whose recess has a trapezoidal shape in cross section, with lateral walls which flair out towards the opening of the recess (c.f. FIG. 8b for example).

The closure member 3 covers the probe over its entire length and in the vicinity of the recess 4 in the probe, has an aperture 5 of dimensions slightly greater than those of the recess. The arrangement of the sample-taking device is slidably mounted in the lateral wall 6 of the flow circuit of the material and in the lateral wall 7 of a sampler attached to the wall 6 of the circuit. The wall 6 defines a sampling region 8, whereas the sampler defines a discharge region 9.

The axial movement is produced by appropriate drive means, such as racks, cams or, in the case of FIG. 2, by a hydraulic or pneumatic ram whose rod 11 acts on the base of the sample-taking device and whose body 12 is pivoted to a foot 13 resting on the frame 14 of the apparatus. The sample-taking device 1 passes through holes provided in the walls of the sampler 9 and sampling region 8, the seal in the region of these holes being ensured by gaskets 15 and 16. The sliding of the sample-taking device is facilitated by the provision of self-lubricating bearings (not shown). Similarly, the probe and closure member must be self-lubricating in order that their relative movements are not hindered. The base of the sampler 9 is constituted by a hopper 17 to which are fitted containers or systems intended to receive or convey the sample, for example a flask 18.

The closure member may be rotated through a predetermined angle, relative to the probe, between a closed position (FIG. 1d) in which it closes the recess 4 and an open position in which the aperture 5 coincides with the recess 4.

Thus, since the sample-taking member 1 is initially stationary, i.e. in the retracted position, obviously directed downwards, the closure member is closed and the sample-taking device is made to penetrate, under the action of drive means such as the ram 12, into the sampling region 8. It will be noted that in order to facilitate the penetration of the sample-taking device into the material to be sampled, the nose 19 of the sample-taking device is slightly tapered. The sample-taking device is then turned through approximately 180° in order to direct the recess 4 upwards, the closure member always remaining closed (FIGS. 1c and 1d). The closure member is then opened (FIGS. 1e and 1f). Thus, the instantaneous automatic filling of the recess is undertaken by simple gravity. The closure member recloses immediately. The sampler is then withdrawn, retaining it in the same angular position and bringing the recess containing the sample into the sampling region 9. The sampling arrangement is then rotated through 180° and the closure member is opened (FIGS. 1a and 1b) which allows the sample to flow by simple gravity into receptacle 18. Finally, the closure member recloses and the sampler is ready for the next cycle.

In the embodiment illustrated in FIGS. 3 and 4, on the rear portion, the probe 2 has a helical groove 19 having an amplitude of 180°, which becomes rectilinear at its ends and in which a lug 20 integral with the support frame for the sampler engages. As may be seen from FIG. 3, the longitudinal pitch of the groove 19 is sufficiently long to facilitate complete penetration of the recess 4 inside the region 8 for taking the sample.

The closure member 3 is also provided with a helical groove 21 which may be superimposed on the groove 19 of the probe. A second fixed lug 22 provided behind the lug 20 in the longitudinal direction is engaged in the grove 21. The lug 20 is longer than the lug 22 in order to penetrate the groove 19 after having passed through the groove 21. Finally, in the region of the end of travel of the lug 20, the helical groove 21 is extended by two notches 23, 24 extending in opposite directions, in the periphery of the closure member and which notches are sufficiently wide to encircle the two lugs 20 and 22.

The operation of the sampler which has been described is as follows:

Starting from the inoperative position in which the sampler 1 is retracted, with the recess 4 directed downwards (FIG. 3) and the closure member closed, a first ram, such as 12, illustrated in FIG. 2 exerts a thrust in the axial direction on the bottom of the sampler. First of all, the arrangement of the probe 2 and closure member 3 penetrates the inside of the sampling region 8, whereas the lugs 20 and 22 retain it along the longitudinal rectilinear portions of the grooves 19 and 21 respectively. Secondly, the arrangement, guided by the cam effect exerted by the lugs on the superimposed grooves 19 and 21, turns through 180° to pass into the sampling position, for which the recess 4 is directed upwards (FIG. 4), the closure member always being closed. Then, a second rotary drive means, an example of which will be described with reference to FIG. 5, rotates the closure member 3 alone to open it, this movement being possible due to the fact that the lugs 20 and 24 are located in the notch 22. At the end of a predetermined period of time, necessary for taking the sample, the rotary drive means recloses the closure member. The ram 12 then retracts the sampling arrangement, which turns through 180°. At the end of travel of the probe, the rotary drive means momentarily opens the closure member, the lugs 20 and 22 thus moving into the groove 23. After emptying the recess 4, the closure member recloses and the sampler is ready to carry out a new cycle.

Figure 5:
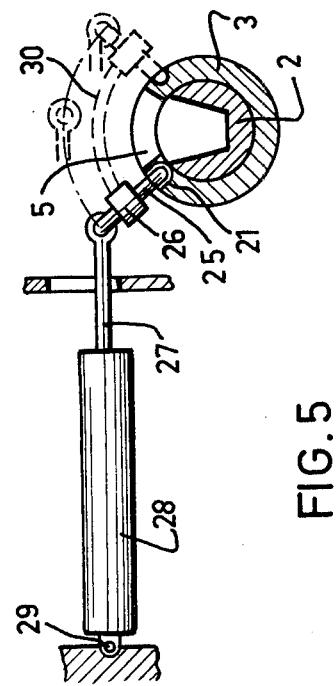
FIG. 5 is a view in radial section with respect to the sampler and showing a device making it possible to rotate the closure member with respect to the probe.

With refernce to FIG. 5, engaged in the helical groove 21 of the closure member 3 is a lug 25 belonging to a member 26 pivoted to the end of the rod 27 of a ram, whose body 28 is pivoted at 29 to the frame of the apparatus. Furthermore, the member 26 comprises a finger member not shown in FIG. 5, which moves in a guide groove 30 concentric to the closure member 3. The travel of the rod is regulated in order that the closure member pivots between two positions, in which it closes and opens the recess of the probe 2.

It is also possible to use a single axial force force for carrying out the reciprocating movements of the probe and rotary movements of the closure member. This force may be exerted by a ram disposed along the axis of the sampling device. On the other hand, the helical groove 15 formed on the closure member should have an angular amplitude greater than 180°, in order that the closure member may continue to rotate alone, once the probe has been immobilized.

The movement of the ram or rams will be controlled by applying electricl pulses to an electric valve which is able to bring the ram into the operating position (thrust). This position thus corresponds to that of taking the sample. A maintaining relay supplied by the same pulse is retarded solely during the time necessary for filling. This time is determined depending on the volume of the recess 9 and on the rate of flow of the material to be sampled. In practice, this delay is between 5 and 15 tenths of a second, for example for wheat. Immediately after this time, as the ram returns to its inoperative position, it returns the sampler to the emptying position. After the return to this position, the sample is transferred to a container. At the end of the predetermined time, another vessel takes the place of the preceding vessel to receive a new sample.

The amplitude which controls the sampling may be produced manually as desired or it may be synchronized with a device for detecting the passage of material, which makes it possible to immediately check the material which arrives at a predetermined point. This same principle of synchronization may be applied, for example, to an automatic weighing balance, which makes it possible to take one or more samples automatically and without human intervention, according to a predetermined programme. Programmes of the frequency of samples to be taken may be either determined statistically and selected in advance or be random.

FIG. 6 shows a device for taking a sample with a fixed closure member 3 integral, for example, with the walls 6 and 7 of the region for taking samples and with the sampler. The aperture 5 of the closure member opens in a downwards direction, for example above a receiving hopper. The probe 2 is initially located in a completely retracted position with its recess 4 directed downwards coinciding with the aperture 5. It may be guided by a system comprising a lug and groove similar to that of FIG. 3.

If the positions and relative dimensions of the recess 4 and aperture 5 are not chosen appropriately, it may happen that the sampler 9 is not airtight with respect to the sampling region 8. Thus, as shown in FIG. 6, when the probe is pushed in the direction of arrow $f$ to take a sample, the recess 4, which is then empty, establishes a connection between the regions 8 and 9. Particles foreign to the sample may thus pass in the direction of arrow $f'$ towards the sampler 9 and, from there, into the vessels fixed to the base of the sampler.

A drawback of this type is eliminated by the sampling devices of FIGS. 7 and 8a. Firstly, referring to FIG. 7, the problem of the seal between the sampling region 8 and discharge region 9 is resolved by giving the tubular portion 32 of the closure member, located between the partition 6 of the region 9 and the aperture 5, a length which is substantially greater than that of the recess 4. In this way, as shown by the position in dot-dash line in FIG. 7, the recess never opens both into the region 8 and region 9.

In the embodiment of FIG. 8a, the sampling device comprises guide means which cause the immediate return of the probe 2, at the beginning of the penetration movement, such that the recess 4 is placed opposite a solid wall of the closure member 3. The guide means are constituted by a groove 33 in the shape of a closed loop, formed in the wall of the closure member and by a radial finger member 34 integral with the probe 6 and engaging in the groove 10. Naturally, the groove may also be formed on the probe and the finger member may be integral with the closure member.

More precisely, starting from the most retracted position of the finger member 34, the groove comprises a short helical portion 35 intended to pivot the finger member from a position (FIGS. 8a and 8b) in which the recess 4 of the probe coincides with the aperture 5 of the closure member, to a position, illustrated in FIGS. 8c and 8d, in which the recess is located opposite a solid wall of the closure member. Taking into account the small pitch of this section, the probe is immediately turned, with only a slight penetration into the sampling region 8. A rectilinear section 36 identical to one generatrix of the closure member, follows the helical portion 35. The section 36 has a length substantially equal to the travel of the probe, such that during penetration, the recess 4 remains in the position of FIG. 8c. The groove is then extended by a second helical portion 37 which moves the recess 4 downwards, at the end of travel of the probe (FIG. 8e), in order to empty the recess of foreign particles which could have been introduced during the penetration, then by a third helical section 38 which turns the probe through 180°, in order to place the recess in the position for taking a sample (FIG. 8f), then by a rectilinear return section 39 whose length is substantially equal to the return travel of the probe and along which the finger member 34 moves in the direction of withdrawal without being deflected and finally, by a helical portion 40 connected to the helical portion 35 and able to turn the probe through 180° after its withdrawal and thus to place the recess in the emptying position (FIG. 8a).

Owing to a device for taking samples of this type, the purity of the sample is preserved during the entire sampling cycle. A single ram, whose rod 19 is visible in FIG. 8a, is sufficient for actuating the sampling device.

During the withdrawal of the probe of a sampling device having a fixed closure member, if no precaution is taken, it may happen that a grain of material of the sample jams between the rear lip of the recess and the tip of the closure member (see FIG. 10).

FIG. 9 illustrates a sampling device devoid of such a drawback. For this, in the sampling region 8, the closure member 1 is extended by a tubular portion 42 whose inner end is bevelled along a sectional plane 43 which is substantially parallel to the path 44 described by the rear lip 45 of the recess, when the finger member 34 travels through the section 40. On the other hand, the sectional plane 43 is set back with respect to said path 44. By an appropriate adjustment, this stagger between the lips 45 and 46 of the recess and closure member may be adapted to the grain size of the product to be sampled. Thus, if a grain jams between the lips 21 and 22, it is normally expelled without being broken, as afore-described.

According to a second solution, which is illustrated in FIG. 10, the portion of probe 47 surrounding the lip 45 and/or the portion of the closure member 48 which surrounds the lip 46 are made from a flexible and deformable material, for example rubber. Owing to their flexiblity, the portions 47 and 48 absorb possible impacts produced at the time of jamming of the grain and thus prevent it from breaking.

According to a third solution illustrated in FIG. 11, on the front portion, located in front of the recess 4, the probe 2 comprises a flat part 49 whose depth is greater than the average size of the grains of material 50. Thus, together with the closure member 3, the probe 2 defines a gap in which several grains of material may be housed with clearance. As aforementioned, the presence of the flat part 49 does not impair the seal between the regions 8 and 9, since the probe is guided to be placed in a sealed position immediately after sampling and after emptying.

If, despite everything, it happens that a jammed grain breaks and that broken material 51 penetrates the recess 4 of the probe (FIG. 12) it is necessary to prevent this broken material from being emptied into the hopper. To this end, it is provided according to the invention that when the probe is completely retracted, the recess 4 projects beyond the aperture 5 of the closure member, adjacent the tubular bevelled portion 42, in order to form with the walls of the closure member and of the portion 42 beyond which it projects, a chamber 52 in which the fraction of sample containing the broken material, remains in the recess and is not allowed to flow. This fraction is expelled into the sampling region during the following operation of the probe.

The sampling device, whose radial section is illustrated in FIG. 13, is more particularly suited to sampling fine powdery and in particular abrasive material. In this sampling device, a radial clearance $d$ is provided between the probe 2 and the closure member 3, in order to allow the grains of material 54 to move freely, without generating frictional forces between the probe and closure member. The seal betweem the sampling region and the discharge region is guaranteed by means of two longitudinal lips 55 made from metal or plastic material, fixed on either side of the recess of the closure member and by annular gaskets which are not shown, fixed to the probe and closure member. Thus, the frictional surfaces between the probe and closure member are reduced to the single regions of contact with the lips 55 and annular gaskets.

Generally, it is advantageous that in the retracted position of the probe, the terminal chamber of the closure member has zero volume, in order to prevent material from being able to pass into said chamber at the end of the sampling cycle. For this, as shown in FIGS. 7 and 8a, the probe must be sufficiently long to fill the inner volume of the closure member. It is also possible to obtain a terminal chamber having zero volume by moving the probe forwards, after the discharge operation, by sufficient length in order that it fills the inner volume of the closure member.

As explained in the preamble, when the material to be sampled flows by gravity, it is necessary to provide adapters appropriate for interrupting the flow of material during sampling. The adapter of FIG. 14 is constituted by a box 57 inserted in a conduit 58 and in which the material flows by gravity. In the box, a stop plate 59 is pivotally mounted about a horizontal shaft 60 running along one wall of the box. The plate is moved by appropriate drive means, such as a ram 61, between an open position illustrated in full line in FIG. 14 and a closed position, illustrated in broken line, in which position it closes off the entire section of passage of the box. In this latter position of the stop plate 59, the flow of material is completely stopped such that the material accummulates in the pocket 62 located upstream of the stop plate. The sampling device 1 is mounted to slide in a sealed manner through an aperture in the box 57, such that the probe may penetrate the pocket 62.

FIG. 15 shows an improved adapter, which makes it possible to prevent congestion of the installation owing to the accidental blocking of the stop plate in the closed position. In this adapter, the stop plate 63 is mounted to pivot about a shaft 64 passing through the inner space of the box 57 and which defines with the walls of the latter, a first section of passage located in the path of the falling material and a second section offset with respect to said path. The plate 63 pivots between its open position, shown in broken line, in which the flow of material is normal and its closed position, shown in full line, in which the first section of passage is closed. The pocket 62 fills progressively with material and when it is completely full, the overflow empties through the second section which is never closed.

I claim:

1. Automatic volumetric apparatus for taking representative samples of granular material comprising a horizontal cyclindrical probe having a recess of trapezoidal section which has an open lateral face forming the larger base of the trapezoid to permit the taking of a sample of pre-determined volume of material, a fixed obturator sleeve slidably and rotatably receiving said probe, said sleeve having an opening facing downwards of a size greater than the recess in the probe and constituting a discharge outlet for the sample of material, sealing means including rectangular seal elements at the edges of said sleeve bounding said opening and in contact with said probe at the outer surface thereof, drive means for axially displacing the probe, and guide means for guiding the movement of the probe under the action of the drive means to cause the probe to move between a retracted position in which the recess in the probe is in a discharge zone and an extended position in which the probe is in a sampling zone, said recess in the probe being in registry with the opening the sleeve only at the time of discharge, and means associated with said probe at the front of said recess for preventing breakage of particles between said probe and said obturator sleeve as the probe moves to said retracted position and transport of broken particles to said discharge outlet.

2. Apparatus as claimed in claim 1 wherein said means for preventing breakage of particles is constituted by a space provided between the front of said recess and the front extremity of the probe, said space having a depth greater than the size of the grains of material to be sampled.

3. Apparatus as claimed in claim 1 wherein said guide means imposes six different movements on said probe, said guide means being constituted by a groove in the form of a closed loop and a radial finger projecting into the groove, the groove and finger being on the probe and sleeve to produce said movement of the probe, said groove including, in the order of travel of the finger, going from the position in which the probe is completely retracted and said recess is turned downwards;

a first helicoidal section of such size and inclination to produce travel of the finger and rotational movement of the probe to move the recess out of registry with said opening and cause the sealing member to ride on the solid portion of the probe while said probe travels axially to bring the end of the probe slightly into the sampling zone, a first rectilinear section extending axially with respect to a generatrix of the sleeve over a distance substantially equal to the distance of penetration of the probe into the sampling zone, a second helicoidal section to turn the probe so that the recess therein faces downwardly to empty the recess of any foreign particles contained therein, a third helicoidal section to turn the probe 180° to cause the recess to face upwardly in a sampling position, a second rectilinear section having a length substantially equal to the distance of penetration of the probe, and a fourth return helicoidal section connected to said first helicoidal section to turn the probe 180° and place the recess in discharge position facing downwardly.

4. Apparatus as claimed in claim 1 further comprising a box in which the granular material flows by gravity, said probe entering said box in said extended position to reach said sampling zone, at least one closing plate pivotably mounted in said box for movement about a horizontal axis between an open position in which the material is free to flow in said box and a closed position in which the flow of material is blocked and a sample of the material can be received in the recess of the probe, said box having a lateral wall with an orifice, said sleeve being fixed to said wall at said orifice, said box having a width at least as great as the length of the recess in the probe.

5. Apparatus as claimed in claim 4 wherein said closing plate has two extreme positions in which said plate has a free end in contact with said box to define two passage sections, one in the path of the flowing material, the other outside said path, said plate in said one position being in the path of the following material leaving the other passage section open.

6. Apparatus as claimed in claim 2 wherein said probe has a flat surface at the bottom of said space.

7. Apparatus as claimed in claim 3 wherein said recess in said probe is out of registry with said discharge opening in the sleeve when the recess faces upwardly and the finger is in said second rectilinear section thereby preventing direct communication between the sampling zone and the discharge zone.

8. Apparatus as claimed in claim 1 wherein said sealing means further comprises annular gasket members secured to said sleeve.

* * * * *